United States Patent [19]
Lai et al.

[11] Patent Number: 4,882,234
[45] Date of Patent: Nov. 21, 1989

[54] STORAGE-STABLE PORPHIN COMPOSITIONS AND A METHOD FOR THEIR MANUFACTURE

[75] Inventors: Jan-Ji Lai, Sunnyvale; Kevin M. Smith, Davis; Bruce W. McCaul, Palo Alto, all of Calif.

[73] Assignee: Healux, Inc., Sunnyvale, Calif.

[21] Appl. No.: 930,160

[22] Filed: Nov. 12, 1986

[51] Int. Cl.$^4$ .................. A61K 31/40; C07D 437/22
[52] U.S. Cl. .................................... 514/185; 540/145
[58] Field of Search ........................ 540/145; 514/185

[56] References Cited

U.S. PATENT DOCUMENTS 4,649,151  3/1987  Dougherty et al. ............ 540/145 X

FOREIGN PATENT DOCUMENTS 8401382  4/1984  PCT Int'l Appl. .

OTHER PUBLICATIONS

J. Natl. Cancer Inst., vol. 26, 1961, The Use and Derivative of Hematoporphyrin in Tumor Detection.
J. Natl. Cancer Inst., vol. 52, 1974, Activated Dyes as Antitumor Agents.
Chemistry in Britain, May 1986, Light and Porphyrins in Cancer Therapy.
Porphyrin Photosensitization Workshop, (PPW).
Porphyrins in Tumor Therapy, Dougherty et al., Plenum Press, N.Y. and London, 1984.
Photochemistry and Photobiophysics, Moan et al., vol. 9, (1985), pp. 253–261.
Progress in Clinical and Biological Research, pp. 301–314, (1984), The Structure of the Active Component of Hematoporphyrin Derivative.

*Primary Examiner*—Richard L. Raymond
*Attorney, Agent, or Firm*—Irell & Manella

[57] ABSTRACT

Carboxyhydroxyporphin compounds such as hematoporphyrin exhibit instability upon warming. However, if this warming is extended and carried out in solution in the presence of a buffer so as to constitute a moderate temperature heat-treatment, a new composition of matter results which contains as much at 95% or more of an ester-linked oligomeric porphin-based material which is exceedingly storage-stable. This composition has superior activity as a photoimaging and photodynamic therapy agent. This process and the products it produces are disclosed. The oligomer products so formed can be formulated into pharmaceutical compositions for use in neoplastic tissue photoimaging and in photodynamic therapy of neoplastic tissues.

12 Claims, 8 Drawing Sheets

FIG. 3A (HP)
FIG. 3B (HPD)
FIG. 3C (PHE)
FIG. 3D (DHE)
FIG. 3E (PHE)

Fig. 5  FORMATION OF PHE AT 95 DEG. (C)

Fig. 6  CHEMICAL STABILITY TESTS OF PHE AND DHE AT THE TEMPERATURE OF 37°C FOR 72 HOURS

Fig. 7

Fig. 8 DECREASE IN PORPHYRIN CONTENT (μG/G) IN SWISS-WEBSTER MOUSE EARS WITH INCREASE IN LIGHT (630nm) DOSE (J/cm²) AS MEASURE OF IN VIVO LIGHT STABILITY

PHOTOTOXICITY RESPONSE EXPRESSED AS MEAN EVANS BLUE INCREASE (%) IN MOUSE EAR TREATED WITH PHOTOSENSITIZER AND LIGHT (100J/cm²)

Fig. 12 THE EFFECT OF PHOTOSENSITIZER DOSE ON THE PERCENTAGE OF LOCALLY CONTROLLED ("CURED") TUMORS

STORAGE-STABLE PORPHIN COMPOSITIONS AND A METHOD FOR THEIR MANUFACTURE

BACKGROUND OF THE INVENTION

1. Field of the Invention

This invention relates to storage-stable porphin compositions, with particular preference to hematoporphyrin-based compositions, their manufacture and their use as photoimaging agents and in photodynamic therapy.

2. Background Materials

Porphins are nitrogen-containing polyheterocyclic compounds which include porphyrins and chlorins. It has been recognized that some porphyrins and chlorins have a natural tendency to preferentially accumulate in neoplastic tissues relative to normal tissue. It has also been recognized that the porphins so accumulated, being colored and/or fluorescent, can serve as imaging agents for detecting the neoplastic masses. The porphin materials themselves often are relatively harmless and nontoxic but when exposed to light in some cases can become very toxic to surrounding tissues. Thus, the accumulated porphins can be preferentially phototoxic to the tumors in which they accumulate. The general technique has come to be known as photodynamic therapy or "PDT". Lasers are the preferred sources of the 630 nm light which is generally employed.

Hematoporphyrin and materials derived from hematoporphyrin have been identified as advantageous materials in this diagnosis technique and therapy. In the 1960's, Lipson and coworkers developed a material known as "hematoporphyrin derivative" ("HPD") having enhanced localization properties. (See, for example, J. NATL. CANCER INST. 26, (1961) 1) Thereafter, Dougherty and coworkers and others applied HPD in combination with light for selective tumor destruction. (See, for example, J. NATL. CANCER INST., 52 (1974) 1333)

A recent article by Hubert van den Bergh appearing at page 430 of the May, 1986 issue of CHEMISTRY IN BRITAIN provides a concise review of the history of this technology. It and the references it reviews describe the early work of Policard (C.R. SOC. BIOL. PARIS, 91, (1924) 1423), Auler and Banzer (ABH. KREBSFORSCH., 53, (1942) 65) and Figge (UNIV. MED. BULL., 26, (1942) 165), which noted that porphins were phototoxic and that this type of compound preferentially accumulated in neoplastic tissues, as well as more recent studies with porphins and in particular HPD as clinically effective anti-tumor agents. A conference entitled "Porphyrin Photosensitization Workshop" held on June 26 and 27, 1986 at the Sheraton Universal City Hotel (hereinafter the "PPW") and the posters there presented also provide a recent overview of the present state of this therapy.

HPD is produced from hematoporphyrin by the process of treating hematoporphyrin with acetic acid and sulfuric acid and thereafter dissolving the acetylated product (referred to as HPA) in alkali to yield HPD. HPD is also referred to in the field by the tradename "Photofrin I" associated with a widely distributed HPD preparation. Workers have made efforts to upgrade the performance of acid-formed conventional HPD by gel filtration purification to give a purified HPD product referred to as "Photofrin II" (see, Dougherty, et al in PORPHYRINS IN TUMOR THERAPY (Andreoni, et al, eds), pp 23-35, Plenum Press, New York and London). Another approach to modifying HPD has involved drying the HPD and then heat-treating the solid at 160° C. for two hours (see Moan, et al PHOTOCHEMISTRY AND PHOTOBIOPHYSICS 9, (1985) 253-261).

HPD is a complex mixture of materials. (See, for example, van den Bergh, CHEMISTRY IN BRITAIN, noted above and G. Bottiroli, Poster "Influence of Interactions with Cellular Structures on HPD Aggregation State" at "PPW") The Photofrin II material is a mixture as well. (See, M.W. Berns, et al, Poster Cellular and Spectroscopic Studies on HPD and Its Components, at PPW) HPD contains at least 15 components (van den Bergh, CHEMISTRY IN BRITAIN, noted above) including hematoporphyrin itself (HP, structure 1, below), protoporphyrin (PP, structure 1, below), dihematoporphyrin ether (structure 2, below) or dihematoporphyrin ester (structure 3, below), and hydroxyethylvinyldeuteroporphyrin (HVD, structure 1, below).

Structure 1

HVD: R =

PP: R =

Porphyrin structures, Abbreviations: HP, hematoporphyrin; HVD, hydroxyethyl-vinyldeuteroporphyrin; and PP, protoporphyrin.

Structure 2

Structure 3

HPD and the Photofrin II material have been the subjects of numerous studies to attempt to unambiguously identify their active components. These studies have been rendered particularly difficult by the facts that (1) porphin type compounds give very indistinct infrared spectra, (2) porphin type compounds tend to aggregate into a variety of forms and conformations, and (3) the porphins of most interest often contain a plurality of each of several functional groups some of which can be in one form or state of combination and some in another.

Various workers in the field have suggested that either or both of the ether of structure 2 or the ester of structure 3 is the primary contributor to HPD activity. (See, for example, European Patent Application 84/1382 and J. Dougherty, et al, "The Structure of the Active Component of Hematoporphyrin Derivative", appearing at PROG. CLIN. BIOL. RES., 1984, 170, 301–314 —which propose Bis-1-[8-(1-hydroxyethyl)-deuteroporphyrin-3-yl] ethyl ether, stucture 2, above; and D. Kessel "Proposed Structure of the Tumor-Localizing Component of Hematoporphyrin Derivative" appearing at PHOTODYNAMIC THERAPY OF TUMORS AND OTHER DISEASES (G. Jori and C. Perria, eds) pp. 1–7, 1985—which proposes the ester of structure 3, above, and B.D. Musselman, et al, Poster, "Ethers and Esters Linked Dimers of Hematoporphyrin in Hematoporphyrin Derivative" at PPW—which proposes a mixture or ether and ester dimers.

Other studies have suggested that the active species in HPD could be an aggregate of porphyrins, such as an aggregate of DHE units or the like. (See, for example, A. D. Ward, Poster, "The Structure, Conformational Changes, and Mechanism of action of Photofrin II, at PPW; G. Bottiroli, et al, Poster, noted above; P. A. Scourides, et al, Poster, "The Nature of Hematoporphyrin Derivative (HPD).Aggregates" at PPW. But, as already noted, difficulties inherent in the porphin materials have rendered illusive a definite answer.

A fourth characteristic of the porphin compounds has also interfered with clear understanding of their exact structure and, more importantly, has interfered with their use as neoplastic tissue imaging and photodynamic therapy agents. This characteristic is that the known preparations are unstable. They vary in composition from preparation to preparation and have been observed to degrade with time to inactive side products. For example, the Photofrin II material when newly prepared contains about 75% of its active species. At room temperature, this material decreases to 50–55% of the total within a few hours. In our hands, HPD or Photofrin II can be purified via membrane filtration techniques to a purity of about 90% active material. Again, this material is seen to degrade to 50–55% active material in less than 24 hours at room temperature. In response to this problem, the Photofrin materials and like porphin-based photoimaging and PDT agents are commonly shipped at dry ice temperature and stored as frozen solids and only warmed to room temperature immediately prior to use.

It is an object of this invention to provide porphin-based (and especially hematoporphyrin-based) preparations which are relatively more thermally and temporally stable than preparations shown in the art and which maintain high levels of active tumor imaging and photodynamic therapy agents. It is a further object of this invention to provide processes for producing such materials and methods of diagnosis and therapy employing such materials.

STATEMENT OF THE INVENTION

It has now been surprisingly found that even though carboxyhydroxyporphin compounds such as hematoporphyrin derivative exhibit instability resulting in a decrease in photoimaging and PDT activity upon warming, if this warming is carried out on solutions of such compounds so as to constitute a moderate temperature heat-treatment, a new composition of matter results which contains as much as 95% or more of an oligomeric porphin-based material which is exceedingly thermally stable. This composition has superior activity as a photoimaging and/or PDT agent.

The present invention can take the form of the process by which these oligomer products are formed. Such a process includes the step of heat-treating a substantially neutral buffered solution of carboxyhydroxyphyrin at a temperature of at least about 30° C. for a time adequate to convert at least about 80% of the carboxyhydroxyporphin to the storage-stable active oligomer product.

In other aspects this invention includes the products of this process. These products can be defined in product-by-process terms as the product which is produced by the process of heat-treating a substantially neutral buffered solution of carboxyhydroxyphyrin at a temperature of at least about 30° C. for a time adequate to convert at least about 80% of the carboxyhydroxyporphin to the storage-stable active oligomer product. The storage-stable active species has been identified as a covalently ester-linked porphin oligomer.

In a preferred embodiment, the preparation process employs a substantially neutral buffered hematoporphyrin-based porphin or a mixture of such porphins as a solution as its feedstock and especially a substantially neutral buffered aqueous solution of hematoporphyrin having a concentration of hematoporphyrin of at least about 0.1% by weight as its feedstock.

In the case of hematoporphyrin-based feedstocks, the product oligomer contains on average about five ester-linked porphin units and is referred to herein as poly(-hematoporphyrin ester) or "PHE". In these products, at least 80% and preferably at least about 90% of its total hematoporphyrin is present as the hematoporphyrin oligomer. The oligomer is characterized as having lambda max peaks at about 400, 503, 535, 572, and 623 nm for its methyl ester and as having major mass spectrum peaks at mass number 2397 and 1802 also for its methyl ester.

In additional aspects this invention provides photoimaging and PDT compositions containing the ester-linked porphin oligomers and methods of diagnosis and treatment employing the same.

DETAILED DESCRIPTION OF THE INVENTION

Brief Description of the Drawings

In this specification and claims, reference will be made to the accompanying drawings in which

FIG. 3 is a group of four HPLC chromatograms run at identical conditions and a fifth run at other conditions, 3a being a chromatogram of a hematoporphyrin starting material;

3b being a chromatogram of HPD;

3c being a chromatogram of the product of this invention resulting from heat-treating the HP starting material analyzed in FIG. 3a;

3d being a chromatogram of a PHE-rich product "Photofrin II"; and 3e being a second chromatogram of the product of this invention.

FIG. 4 is a group of three HPLC chromatograms run at identical conditions, 4a being a chromatogram of dried HPD;

4b being a chromatogram of dried HPD heat-treated in accord with prior art teachings; and 4c being a chromatogram of a PHE-rich product resulting from heat-treating the hematoporphyrin starting material analyzed in FIG. 3a.

DESCRIPTION OF PREFERRED EMBODIMENTS

Starting Material

The starting material employed in the present invention is selected from the carboxyhydroxyporphins. A carboxyhydroxyporphin is a defined to be a porphyrin or dihydroporphyrin (chlorin) having at least one carboxy and at least one hydroxy substituent on the periphery of its porphin ring. Such materials can contain up to about three carboxyls and up to about three hydroxyls. Representative materials include photoprotoporphyrin, the hematoporphyrin compounds, bacteriopheophorbides c, d, and e; 2-(hydroxyethyl)-pheophorbides derived from pheophorbide a, 2-(hydroxyethyl)-chlorins derived from pheophorbide a (e.g., chlorin $e_6$). The 2-(hydroxethyl) groups can be fashioned from the naturally occurring 2-vinyl substituents by standard hydration reactions familiar to those in the art. Alternatively, 2-acetyl substituents can be reduced to 2-(hydroxyethyl). The term "hematoporphyrin compounds" as used herein includes hematoporphyrin itself, hydroxyethylvinyldeuteroporphyrin, hematoporphyrin derivative, and the forms of hematoporphyrin derivative sold as Photofrin I and II and the monohydroxyethyldeuteroporphyrins. The hematoporphyrin compounds constitute a preferred group of feedstocks. Hematoporphyrin itself is an especially preferred feedstock material. Mixtures of two or more of such starting materials can be used, if desired.

Hematoporphyrin is derived from the naturally occurring compound, heme, and is available commercially from, for example, Aldrich Chemical Company. The material is available in its protonated HCl salt form as a dry powder and as a suspension/solution. The other suggested starting materials are also known compounds which are either available commercially or can be prepared by methods taught in the art.

Any form of hematoporphyrin or the other starting materials can be used. It should be noted, however, that the final product of this invention can find use as an injectable pharmaceutical. Thus, it is advantageous that the starting hematoporphyrin or other starting material be substantially pure and free of toxic or immunologically reactive substances as this makes it possible to employ the product directly with a minimum of purification. Generally, hematoporphyrins that are at least about 80% pure are preferred with materials having a hematoporphyrin content of at least about 90% being more preferred.

The Preparation Process

The process of this invention involves heat-treating a buffered solution of carboxyhydroxyporphin starting material. The buffered carboxyhydroxyporphin is characterized by having a substantially neutral pH that is a pH of from about 5 to about 9, and preferably from about 6 to about 8. Excellent results are achieved with pH's in the range of from about 6.5 to about 7.5 and thus these pH's are particularly preferred. Such pH's can be obtained by the use of suitable buffers. Without buffers, the acidic carboxyhydroxyporphin can lower the pH to outside of the desired range. If, as is preferred, the carboxyhydroxyporphin is used as a solution, these conditions provide good solubility levels.

The phosphate buffer system ($KH_2PO_4$/$Na_2HPO_4$) is generally preferred but any physiologically acceptable buffer yielding the desired pH's can be used. As used throughout this specification and claims, the term "physiologically acceptable" is an adjective which defines a material which can be incorporated in a pharmaceutical such that the pharmaceutical can be injected into a mammalian patient without giving rise to adverse reactions in the patient. Representative physiologically acceptable buffers include, without limitation, the phosphate buffer system just described and its physiologically acceptable alkali metal equivalents, the citrate buffer system (citric acid/sodium citrate) and its physiologically acceptable alkali metal equivalents, the "tris" buffer system, the acetate buffer system (acetic acid/sodium acetate) and its physiologically acceptable alkali metal equivalents, the carbonate buffer system (sodium carbonate/sodium bicarbonate) and its physiologically acceptable alkali metal equivalents and the like. The buffer is dissolved along with the carboxyhydroxyporphin.

The solution of carboxyhydroxyporphin is an aqueous solution. This solution has a concentration of carboxyhydroxyporphin in the range of from the maximum solubility of carboxyhydroxyporphin which is in the range of 2-3% by weight, depending on the temperature and pH of the solution, to a lower level of about 0.1% by weight. Preferred concentrations, especially for the hematoporphyrin compounds, range from about 0.1% by weight to about 2.0% by weight. Although lower concentrations can be used and are included within the scope of the present invention, they are not seen to offer significant advantages. More preferred concentrations are in the range of from about 0.10% by weight to about 1.5% by weight.

The time and temperature employed for the heat-treatment are related. Higher temperatures employ shorter times while with lower temperatures longer times are called for. The temperature is a moderate temperature, especially from about 30° C. to about 150° C. Typical times for the heat-treatment range from one hour to about 400 hours. The time and temperature employed should be adequate to convert at least about 80% and preferably at least about 90% of the starting carboxyhydroxyporphin to the oligomer product. This conversion can be monitored by such techniques as HPLC (high performance liquid chromatography) and ultraviolet spectral analysis. Examples of times and temperatures which give the desired conversions are about 1 hour at 150° C., 5 hours at 120° C., 10 hours at 105° C., 20 hours at 95° C., and 40 hours at 85° C. and 100 hours at 60° C. Preferred time and temperature ranges are times of from about 5 to about 100 hours and temperatures of from about 60° C. to about 120° C. More preferred time and temperature ranges are times of from about 10 to about 40 hours and temperatures of from about 85° C. to about 105° C. Prolonged excess heating is to be avoided, as it can lead to decomposition of the desired product.

The heat-treatment can be carried out in a substantially inert environment such as in a noncatalytic container. Glass containers work well and other inert surfaces which do not complex with the porphyrin structure can also be used. The solution can be capped during heat-treatment with an inert gas such as argon or nitrogen, if desired, or alternatively, the heat-treatment vessel can be closed to prevent substantial access to air, if desired. The conditions of treatment should prevent the introduction of pyrogens into the product. The solution can be agitated during heat-treatment, if desired.

It is an advantage of the present invention that the product as produced does not contain any appreciable adverse by-products which must be separated. The product when produced as a solution can be used as produced with minor work up such as microfiltration to remove any suspended solids and adjustment as needed in pH, isotonicity, concentration, and the like to give a consistent injectable liquid. The carboxyhydroxyporphin oligomers can be recovered as solids by precipitating them from solution by acid addition. HCl or a like mineral acid is a suitable acidulent. Alternatively, the solids could be recovered by evaporating the solvent such as by freeze-drying or the like. The solids so recovered can be dried and stored.

The Product

The oligomer product of this invention can be defined as being the product of the above-described heat-treatment process. It can also be described in terms of its chemical make-up and properties. Although not understood with certainty, it is believed that the product is a mixture of covalently linked carboxyhydroxyporphin oligomers. The bond between the porphin units is believed to be an ester bond. The number of units in the oligomeric chain is on average from about 3 to about 7. The product is a mixture of ester-linked porphin (or in the case of the preferred embodiments, hematoporphyrin) dimers, trimers, tetramers, pentamers and the like. It is a property of the present product that it contains at least about 80% by weight, preferably at least about 90% by weight, and more preferably at least about 95% by weight of its total porphins as the ester-linked oligomers.

It is known that hematoporphyrin dehydrates to form protoporphyrin at high temperatures. By comparison with known samples of protoporphyrin, it has been found that the present product produced from hematoporphyrin does not contain detectable amounts of this material. Likewise, the present material produced from hematoporphyrin is different than the product which results if protoporphyrin is polymerized.

The products of this invention are most uniquely characterized by their superior stability. While various generic porphyrin aggregates have been identified in hematoporphyrin derivative preparations and fractions heretofore these aggregates or high molecular weight porphyrins (HMWP) are only present even with purification and isolation in levels up to about 75%. We have, through filtration, been able to get HMWP levels of as high as 88%. However, the characteristics of the previously identified HMWP materials differ from those observed with the present ester-linked oligomers. These prior materials are quite unstable. At 37° C., a 75% pure solution of the HMWP materials decomposes to about 55% purity within 10 hours. In contrast, the present materials show no changes at room temperature or 37° C. over a time period of 1440 hours.

As will be demonstrated in the examples, the present ester-linked oligomer product can also be distinguished by the unique visible spectrum of its methyl ester and its retention times in HPLC analyses.

Figure 1:
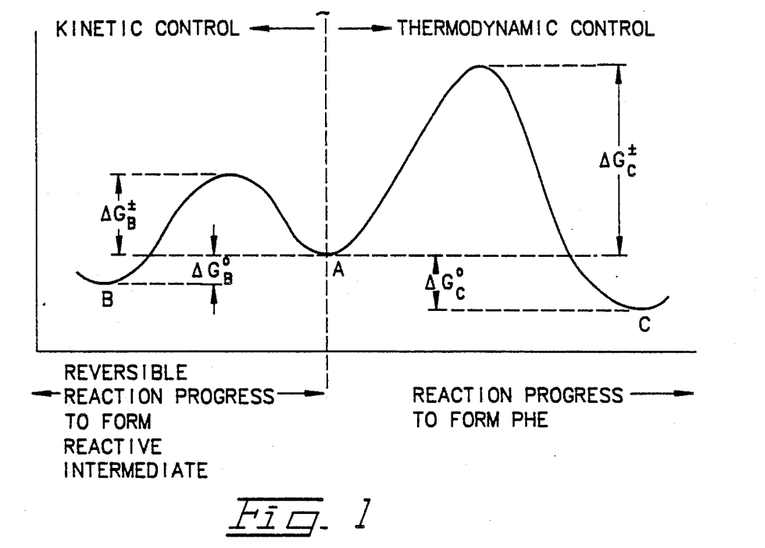
FIG. 1 is an energy diagram depicting the reaction sequence which takes place during the present process.
Figure 2:
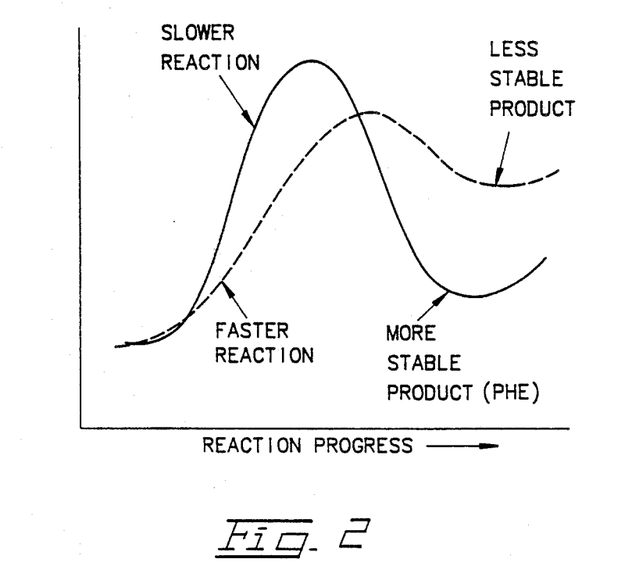
FIG. 2 is an alternative presentation of the energy diagram of FIG. 1 illustrating that the present sequence is an exception to the Hammond Postulate regarding reaction rates and product stability.

Without intending to be bound to any particular theory of how the present invention works, it is now believed by the present inventors that this invention relies upon a series of reactions to yield the product here desired. In the first reaction, the carboxyhydroxyporphin (for example, hematoporphyrin) is rapidly but reversibly converted to an active but unstable species. Simultaneously, at the conditions of the heat-treating of this invention, a second slower reaction is taking place gradually but substantially irreversibly converting the carboxyhydroxyporphin (for example, hematoporphyrin) to a more stable material which is the oligomeric ester of this invention. The first product, being unstable, reverts to the original feed species and eventually is converted to the desired product of this invention by the second reaction. This theory can explain how the present invention can provide a 95%+ pure product which is stable and the prior art products decompose rapidly. To use the language found on pages 421 and 422 of ORGANIC CHEMISTRY, by John McMurry, Brooks/Cole Publishing Company, Montery, Calif., 1984, the first reaction is under kinetic control while the second is under thermodynamic control The above theory describes a pair of reactions which are exceptions to the Hammond postulate (see pages 148-151 of the McMurry text) in that the faster reaction leads to a less stable product and the slower reaction leads to a more stable product. FIGS. 1 and 2 illustrate two reaction energy diagrams for this situation.

PHARMACEUTICAL PREPARATIONS

The carboxyhydroxyporphin oligomer product of this invention can be formulated into pharmaceutical preparations for injection. Such preparations can contain from about 0.1 to about 0.5 grams per liter of the PHE material in a pharmaceutically acceptable nonpyrogenic aqueous injection vehicle. Typical preparations have pH's between about 6.5 and about 7.5 and are isotonic. They also are substantially free of any solid contaminants. The concentration, pH and ionic strength of the preparations can be adjusted by removing water by ultrafiltration, by adding liquids such as sterile water for injection, sterile saline for injection or bacteriostatic water for injection as these liquids are defined in the book REMINGTON'S PHARMACEUTICAL SCIENCES, 1985, Mack Publishing Company, 1985, by adding pH adjusting materials such as U.S.P. sodium hydroxide or U.S.P. phosphoric acid, or the like. The pharmaceutical preparations are then packaged under sterile conditions in suitable vials, bottles, prefilled syringes, and the like for administration via intravenous infusion or intramuscular injection to patients.

Use of the Products

The carboxyhydroxyporphin oligomer components of the products of this invention have the property of being preferentially absorbed into tumor masses. Once accumulated into these masses, the carboxyhydroxyporphin oligomers, being colored and fluorescent, can serve to identify the tumor masses, that is serve as tumor imaging materials, and also can serve as agents for photodynamic therapy. The amount of carboxyhydroxyporphin oligomer material administered to the patient can range from about 0.1 mg to about 10 mg per kilogram of body weight, with amounts of from about 0.25 mg to about 8.5 mg per kilogram of body weight being preferred. In the case of the preferred hematoporphyrin-based oligomer products, preferred amounts are from about 0.25 mg to about 7.5 mg per kilogram of body weight, with amounts of from about 0.50 mg to about 5 mg and especially from about 1 mg to about 3 mg per kilogram of body weight being more preferred. As will be seen in the examples, the present materials are more effective, on an equivalent weight basis, than the materials disclosed in the art. Accordingly, as a general rule, one can expect to use somewhat smaller doses of the present materials than are called for with materials of the art.

These materials are administered either as a single injection dose or as a more prolonged infusion. In either case, it is desirable to permit the agents to accumulate in the neoplastic tissues after administration. This can take from about 1 to about 5 days with preferred accumulation times ranging from about 1 to about 3 days. After the oligomers have accumulated in the neoplastic tissue they are rendered photodynamically active by irradiation with light. Typical irradiation doses range from about 25 to about 200 joules/cm$^2$ with preferred doses being in the range of from about 50 to about 100 joules/cm$^2$. Lasers, especially 630 nm wavelength lasers, are a preferred source of the irradiation dose.

Due to Food and Drug Administration regulations, the present oligomers have, to date, only been tested in animal models. The animal models chosen are known to be relevant to human therapy and on this basis it is believed that the present materials will yield equivalent favorable results in humans.

The invention will now be further described with reference to the following Examples. These are presented solely to make clear preferred embodiments of the present invention and are not to be construed as limiting the scope of the invention which is as defined by the appended claims.

EXAMPLE 1

A. Preparation of PHE

NaOH(s) (18.00g) and KH$_2$PO$_4$(s) (68.80g) are dissolved in 3600 ml of sterile water to yield a pH 7.2 buffer solution. Hematoporphyrin (HP, commercially available) (27.50g) is then added to the buffer and stirred at room temperature until the HP dissolves completely. The solution is then placed in an inert walled (glass) container and this container is sealed and in turn placed in a metal container and placed in an oven preheated to 95° C. After 20 hours, the solution is removed from the oven and cooled to room temperature. Samples are withdrawn periodically and analyzed to detect the disappearance of HP and the appearance of PHE and other products. The analysis employs an HPLC using a Perkin Elmer Pecosphere C$_{18}$ column (4.6×150 mm), an absorbance detector set at 390 nm and a programmed solvent flow of 1.1 ml/minute and the following two programs:

| Step | Solvent | Program 1 | Program 2 |
|---|---|---|---|
| 1 | Solvent A | 8 minutes | 25 minutes |
| 2 | Lin. grad to sol B | 8 minutes | 15 minutes |
| 3 | Solvent B | 5 minutes | 5 minutes |
| 4 | Lin. grad to sol B | 8 minutes | 5 minutes |
| 5 | Solvent C | 5 minutes | 5 minutes |
| 6 | Step grad to sol B | 5 minutes | 5 minutes |

Solvent A methanol/water 80/20% with 0.09% w/V NaCl
Solvent B methanol/water 80/20%
Solvent C methanol 100%

In these analyses, the various materials of interest have the retention times as shown in Table 1.

TABLE 1

| | Retention Times, minutes | |
|---|---|---|
| Compound | Program 1 | Program 2 |
| HP | 2.00–2.50 | 2.00–2.50 |
| HVD | 4.50–5.00 | 4.50–5.00 |
| — | 5.50–6.00 | 5.50–6.00 |
| PP | 19.00–19.50 | 22.57–22.82 |
| PHE | 18.00 and up | 39.00 and up* |

Note: The retention time for the majority of PHE is between 18.00 and 22.00 minutes with Program 1 and between 39.00 and 44.00 minutes with Program 2.

Figure 3A:
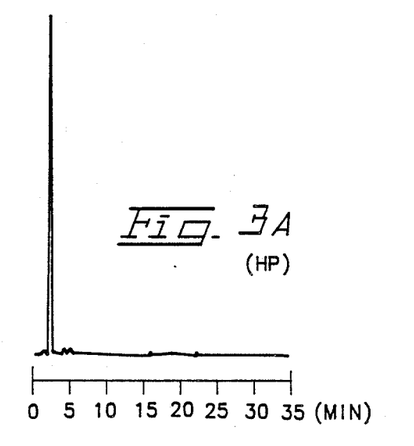
Figure 3B:
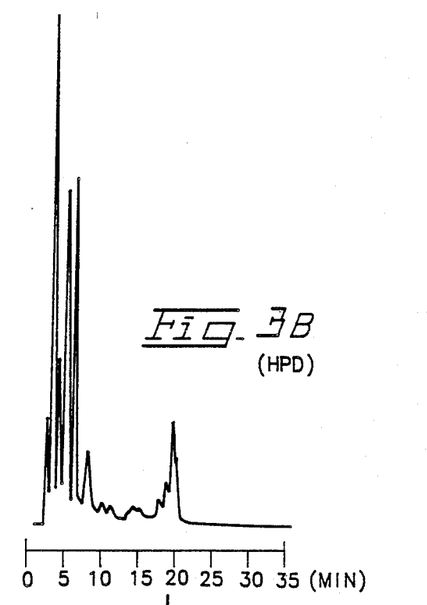
Figure 3C:
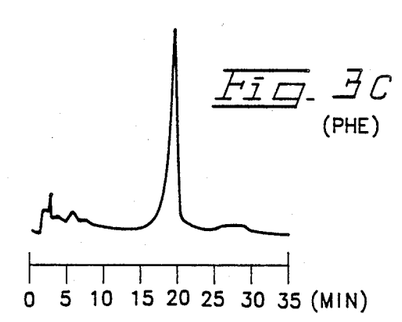
Figure 3D:
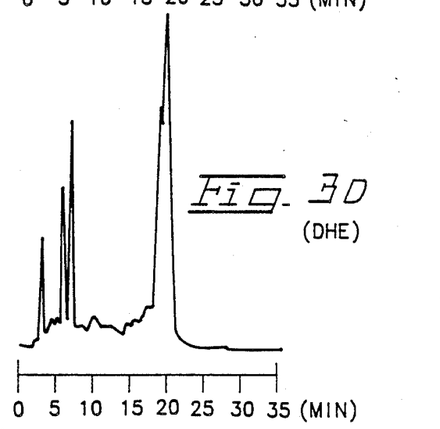

FIGS. 3a and 3c are program 1 HPLC chromatograms for the HP starting material and the PHE-rich product after 20 hours of heat-treatment. These curves show unambiguously that the HP feed is converted to the PHE product.

Figure 5:
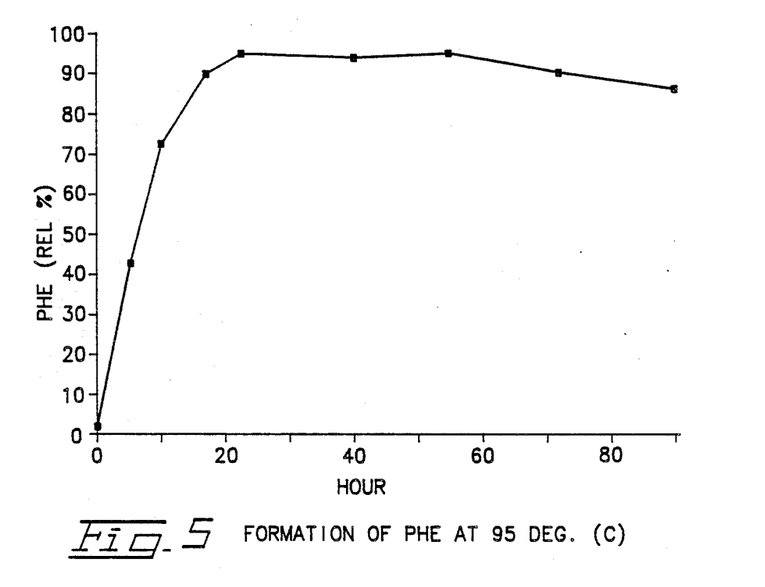
FIG. 5 is a graph illustrating the appearance of PHE in a hematoporphyrin feedstock as a function of heat-treatment at 95° C. for various times.

FIG. 5, a graph arising from an earlier time vs conversion study in the same reaction system, the amount of PHE rises with time, reaching over about 95% of the total hematoporphyrin started with in about 20 hours and after about 60 hours of heating a gradual drop in the amount of PHE is noted.

The absolute concentration of the PHE in the solution is determined using a nitrogen analyzer and confirmed to account for over 95% of the original carboxyhydroxyporphin fed.

B. Formulation of the Product

The concentration of the product of part A is then adjusted with isotonic sterile saline solution to yield a final concentration of 2.5 mg/ml.

The solution is aseptically charged to 30 cc vials using a sterile 0.22 micron filter (Millex GS or Sterivex-GS type) and the vials are closed with aluminum crimp caps. This provides a series of dosage forms of the PHE product in a formulation suitable for injection.

C. Properties of the PHE Product

Figure 6:
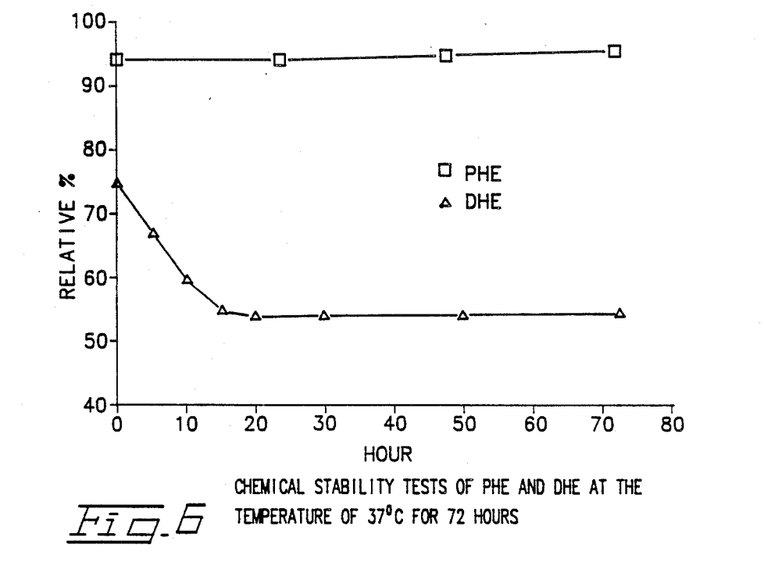
FIG. 6 is a graph of the composition of a material of this invention and a material of the art as a function of time at 37° C. illustrating the superior stability of the products of the invention.

The PHE product of part A of this example is studied to determine its properties. The first two distinctive properties observed are the high purity and stability of the PHE product. As reflected in FIG. 5, the PHE product has a PHE purity of greater than 95% and a substantial stability at temperatures as high as 95° C. In contrast, the known "hematoporphyrin dimer ether" (DHE), which is the predominant material in the widely-tested Photofrin II product, has a maximum purity of only slightly greater than 70% and when exposed to temperatures as modestly elevated as 37° C. drops to a purity of about 55% in about 20 hours. This instability is illustrated in FIG. 6 which is a graph of the composition of a DHE sample as a function of time when exposed to 37° C. Consistent results are also obtained when a sample of this "dimer ether" product is purified to 88% purity and permitted to stand at 37° C. FIG. 6 includes a stability curve for the present product under the same conditions which shows that there is virtually no drop impurity over the same period and even out to as much as 1440 hours.

A third distinctive property of the PHE material is its HPLC chromatogram. A sample of the "20 hour" product of part A is analyzed by HPLC using the apparatus and column described in part A. A four solvent elution is used according to the following schedule.

| Step | Solvent | Time Eluted |
|---|---|---|
| 1 | Solvent A | 15 minutes |
|  | Step grad. to sol B |  |
| 2 | Solvent B | 10 minutes |
|  | Step grad. to sol C |  |
| 3 | Solvent C | 5 minutes |
|  | Step grad. to sol D |  |
| 4 | Solvent D | 5 minutes |
|  | Step grad. to sol C |  |
| 5 | Solvent C | 10 minutes |

Solvent A methanol/water 80/20% with 0.09% w/V NaCl
Solvent B methanol/water 80/20% with 0.006% w/V NaCl
Solvent C methanol/water 80/20%
Solvent D methanol 100%

Figure 3E:
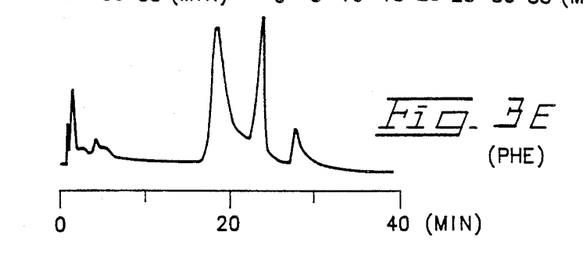

The results of this analysis are given in FIG. 3e and show a series of three major components. The largest and fastest moving of these appears at about 16-18 minutes and constitutes about 80% of the total mass of the sample. The second and third peaks elute at about 23 and 28 minutes respectively, under the conditions of analysis, and constitute about 10% and 10% of the total mass respectively.

A fourth characteristic of the PHE product is the visible spectrum of its methyl ester (formed by the diazomethane method) in $CH_2Cl_2$ which exhibits λ max values at 400, 503, 535, 572, and 623 nm. The diazomethane method involves, in a representative reaction, the following: a 200 ml quantity of the PHE/PBS solution of part B (2.5 mg/ml concentration) is treat with 1N HCl (aqueous) dropwise until the pH is between 2.5 and 3.0. A brown precipitate forms which is collected, washed with ether and dried. (This constitutes a recovery of a dry PHE product.) Yield is about 480 mg of this product. To 260 mg of this solid product in 100 ml $CH_2Cl_2$ is then added 50 ml of a methanol/ether solution of diazomethane. the resulting mixture is then stirred at room temperature for three hours. Then the solvent is evaporated off at reduced pressure and the residue is recrystalized from $CH_2Cl_2$/n-hexane to yield the desired methyl esters in 255 mg yield.

A fifth characteristic of the PHE product is the fact that its methyl ester is very soluble in organic solvents such as $CH_2Cl_2$, THF, ether and the like.

A sixth characteristic of the PHE product is its solubility in common solvents. It gives a brown precipitate in pH 2-5 water. This solid is fairly soluble in methanol and ethanol but relatively insoluble in methylene chloride and ether.

Figure 7:
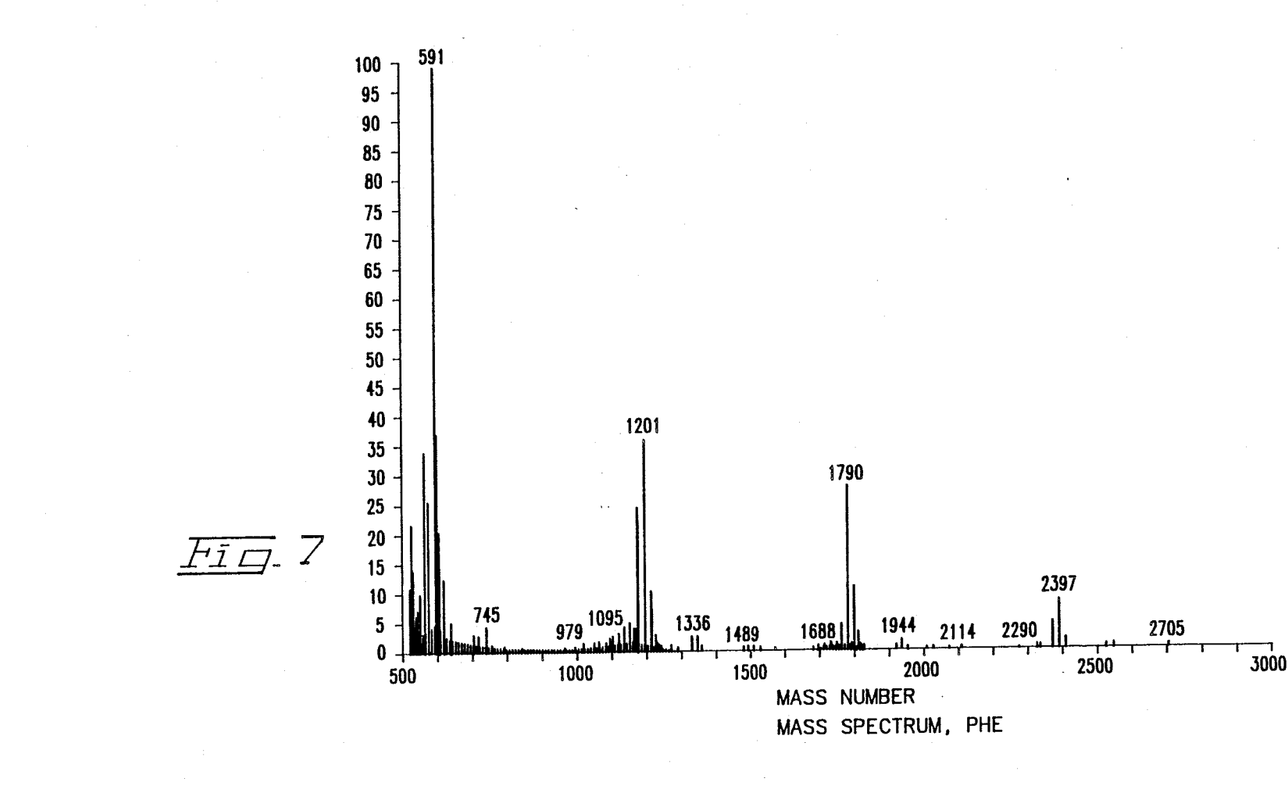
FIG. 7 is a mass spectrum of a material of the present invention.

A seventh characteristic of the PHE product is the mass-spectrum of its methyl ester. A typical spectrum is given as FIG. 7 and exhibits primary peaks at mass number 2397, corresponding to the tetramer fragment of hematoporphyrin oligomer ester methyl ester and at mass number 1802, corresponding to the trimer fragment of hematoporphyrin oligomer ester methyl ester.

EXAMPLE 2

The preparation of Part A of Example 1 is substantially repeated with several changes in the reaction conditions. The starting solution contains

| | |
|---|---|
| Hematoporphyrin·HCl | 10.17 g |
| NaOH | 6.64 g |
| $KH_2PO_4$ | 25.48 g |
| NaCl | 30.66 g |
| $H_2O$ | 3600 ml |

This material has a pH of about 7.2. When heated at 95° C. for 21 hours it would yield a product having a purity of 96% of the desired ester-linked hematoporphyrin oligomers.

EXAMPLE 3

The preparation of Part A of Example 1 is substantially repeated with several changes in the reaction conditions. The starting solution contains

| | |
|---|---|
| Hematoporphyrin·HCl | 70.0 g |
| NaOH | 46.0 g |
| $KH_2PO_4$ | 174.1 g |
| $H_2O$ | 10000 ml |

This material has a pH of about 7.15. When heated at 95° C. for 25 hours it would yield a product having a purity of 95% of the desired ester-linked hematoporphyrin oligomers.

EXAMPLE 4

The preparation of Part A of Example 1 is substantially repeated with several changes in the reaction conditions. The starting solution contains

| Hematoporphyrin·HCl | 85.0 mg |
| NaOAc | 1.5 g |
| H₂O | 30 ml |

This material has a pH of about 7.05. When heated at 95° C. for 20 hours it would yield a product having a purity of 95% of the desired ester-linked hematoporphyrin oligomers.

EXAMPLE 5

The preparation of Part A of Example 1 is substantially repeated but at a higher reaction temperature of 125° C. instead of 95° C. At this temperature, the product contains over 90% PHE after 4 hours.

EXAMPLE 6

The preparation of Part A of Example 1 is substantially repeated twice but at lower reaction temperatures of 80° C. and 55° C. instead of 95° C. The reactions are stopped prior to reaching the desired 90–95% purity but the analysis of periodic samples indicates that the desired oligomer esters are in fact forming at these temperatures. The rates of formation which are observed will result in the 90–95% level being reached in about 50 hours at 80° C. and about 200 hours at 55° C.

EXAMPLE 7

The preparation of part A of Example 1 is substantially repeated with several changes in the reaction conditions. Instead of hematoporphyrin HCl, lyophilized hematoporphyrin derivative is employed. The starting solution contains

| HPD (lyophilized) | 300 mg |
| NaOH | 178 mg |
| KH₂PO₄ | 816 mg |
| NaCl | 1.08 mg |
| H₂O | 40 ml |

This material has a pH of about 7.4. When heated at 95° C. for about 20 hours it would yield a product having a purity of over 90% of the desired ester-linked hematoporphyrin oligomers.

EXAMPLE 8

COMPARATIVE EXPERIMENT

Figures 4A, 4B, 4C:
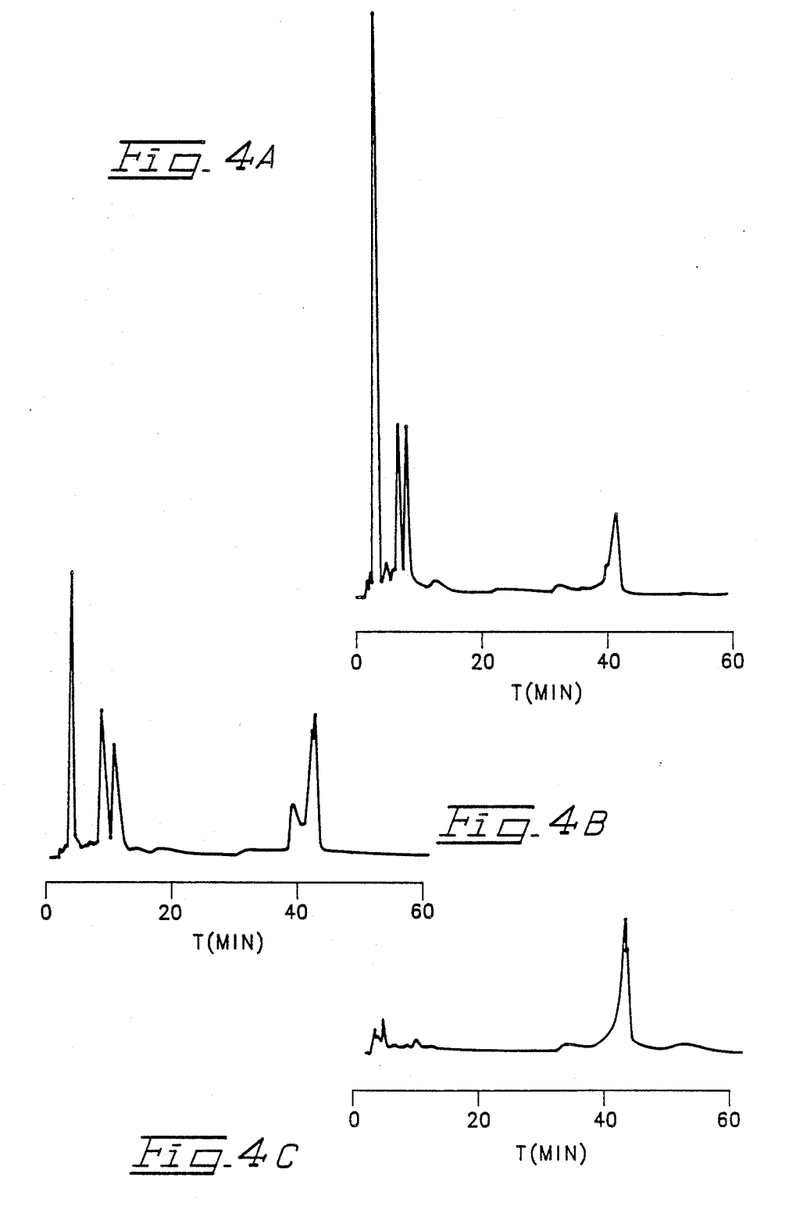

The experiment of Moan et al PHOTOCHEMISTRY AND PHOTOBIOPHYSICS 9 (1985) 253–261 is repeated. In this experiment dry HPD is heated at 160° C. for 2 hours. The results of the experiment show that the resulting product is different than the present invention. This is shown in FIG. 4 in which a is a chromatogram of redissolved dry HPD, b is a chromatogram of dry HPD which has been heated at 160° C. for 2 hours and c is a chromatogram of a product of this invention.

Biological Properties Of The Oligomer Product

The biological properties of the PHE "20 hr" product of part A of Example 1 and two similar products prepared in accord with the general teachings of Examples 1 through 5 are determined through in vitro photodynamic activity tests and in vivo tests. These results are compared with the results obtained in similar tests run on the HPD and purified HPD materials promoted under the names "Photofrin I and II".

The in vitro test of the relative photodynamic activity of three PHE preparations and the two HPD materials is carried out in the following five aqueous solutions: pH 7.4 phosphate buffer (PBS), 20 mg/ml collagen dispersion in PBS, 10% fetal serum in PBS, tetrahydrofuran:sodium dodecal sulfate (30:70 THF:SDS, 0.07 M SDS), and cetyltrimethyl ammonium bromide (CTAB, 0.01M) in PBS. The quantum yields of oxygen uptake (moles of oxygen consumed/Einsteins of photons (630 nm) absorbed) are calculated from the initial slopes of the oxygen uptake curves as measured by a recording oxygen electrode system. All five materials show photodynamic activity but are relatively poor photosensitizers in PBS. The highest yields found are with CTAB.

Figure 8:
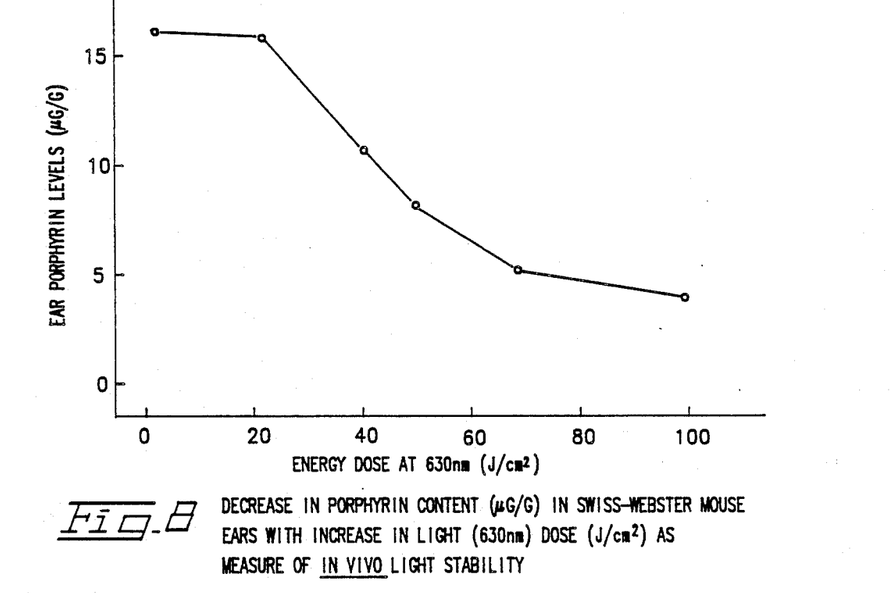
FIG. 8 is a graph showing in vivo light stability for compounds of the invention.

The in vivo light stability is measured by administering the oligomeric products of this invention to Swiss-Webster mice, allowing the materials to circulate, exposing the mice ear tissues to various 630 nm light doses and thereafter measuring the porphyrin content of the mouse ear tissues. The study shows that the in vivo light stability depends on the light dose as shown in FIG. 8. At 60 J/cm² porphyrins in mouse (Swiss-Webster) ear skin are reduced by about 50%. This is true of other HPD preparations also.

The in vivo testing of photosensitizer preparations for tumor phototherapy is dependent on several factors including tumor type, host species and condition, photosensitizer type and dose, light and light dose and other therapeutic interventions. The in vivo assessment of the PHE material uses the mouse S180 tumor growing as a solid tumor implant in Swiss-Webster (SW) albino mice. The Cooper Lasersonics Aurora-Lexel Argon-dye laser is used as a light source.

A primary issue in the assessment of a photodynamic agent is the relative efficiency of photosensitizer localization and retention in tumor and other tissue. Porphyrin levels are determined for three materials of this invention and compared with results obtained with the two "Photofrin" materials in tumor and several tissues using the extraction-fluorescence assay method for total porphyrins as is described by Straight and Spikes in METHODS OF PORPHYRIN PHOTOSENSITIZATION, Plenum Press, New York, 1985, pp. 70–90. The levels determined are shown in Table 2.

| PHOTOSENSITIZER (μG/G) LOCALIZED/RETAINED | | | | | |
| --- | --- | --- | --- | --- | --- |
| Photosensitizer Localization/Retention Total porphyrin content of tissues from Swiss-Webster mice (mean values for five mice) extracted 48 hrs after intraperitoneal injection of a dose of 40 mg/kg. | | | | | |
| Tissue | PFI | PFII | PHE (1) | PHE (2) | PHE(3) |
| Brain | 23 | 35 | 127 | 77 | 60 |
| Ear | 11 | 20 | 67 | 48 | 56 |
| Heart | 45 | 61 | 96 | 111 | 171 |
| Kidney | 59 | 72 | 103 | 106 | 93 |
| Liver | 740 | 533 | 733 | 682 | 577 |
| Lung | 110 | 140 | 149 | 204 | 285 |
| Muscle | 61 | 80 | 43 | 87 | 91 |
| Gonads | 109 | 163 | 217 | 190 | 178 |
| Spleen | 94 | 124 | 142 | 198 | 256 |
| Tumor | 42 | 69 | 74 | 85 | 118 |

It is noted that the PHE preparations result in higher tumor and tissue levels compared to Photofrin I and Photofrin II. This is especially interesting in view of the fact that the PHE materials exhibit lower skin phototoxicity and higher tumor phototherapeutic effectiveness. It may suggest a different retention/photodynamic mechanism in normal skin vs tumor. Frozen section histology-fluorescences microscopy of tumor sections show a similar distribution pattern for the several preparations of PHE. HPLC chromatograms are run on porphyrins extracted from tissue (liver, spleen) and tumor (S180) from mice (Swiss-Webster) injected with PHE. The data show that the materials which are extracted are similar to what was injected. Thus the PHE appears to remain intact in vivo.

Dark toxicity of PHE preparations is evaluated in terms of mouse $LD_{50}$ assay using the method of Karber,. (1931) ARCH. EXP. PATH. PHARMAK. 162, 480. The results obtained are given in Table 3

TABLE 3

Dark Toxicity of Photosensitizers

| Photosensitizer | $LD_{50}$ Dose, mg/kg |
|---|---|
| Photofrin I | 185 |
| Photofrin II | greater than 200 |
| PHE | greater than 200 |

Figure 9:
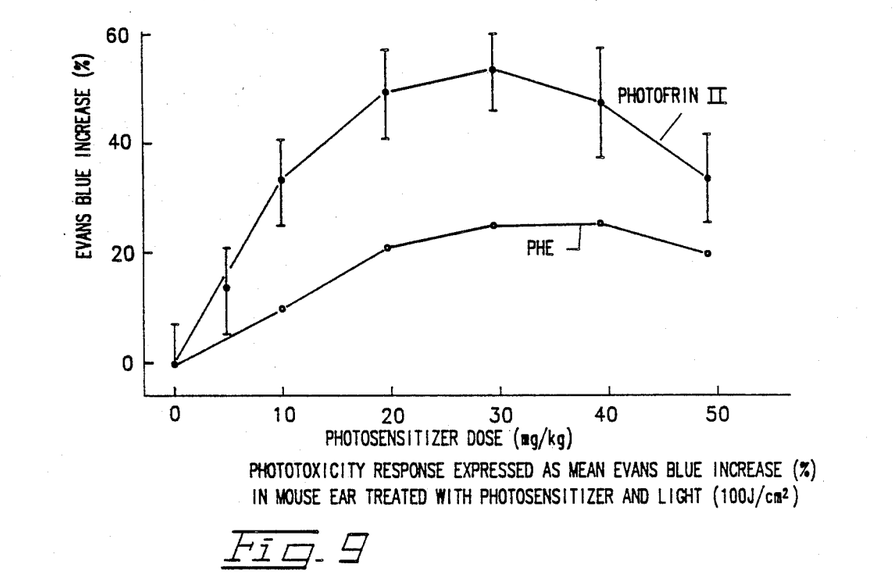
FIG. 9 is a graph comparing the phototoxicity of a composition of this invention with that observed with a material of the art.

The major side effect of hematoporphyrin derivative preparations in tumor phototherapy is the extended phototoxicity to normal skin (by way of the exposed skin vasculature) for a month or longer after injection of therapeutic doses. The phototoxicity to normal skin vasculature of PHE is evaluated in the ear of albino Swiss-Webster mice using Evans blue assay method and compared to results obtained with other HPD preparations and other photosensitizers (zinc phthalocyanine sulfonate, ZPS; tetraphenyl porphyrin sulfonate, TPPS; and methylene blue (Mb)). The results are shown in Table 4 and FIG. 9.

TABLE 4

Photosensitizer Phototoxicity In Swiss-Webster Mice.
The minimum effective dose (M.E.D.) of Photosensitizer required to damage the albino mouse ear vasculature sufficiently to cause a statistically significant ($P < 0.05$) increase (%) in Evans blue extravasated through the damaged vascular wall into ear tissue 24 hrs after irradiation with Cooper Laser Sonics Aurora-Lexel Argon Dye Laser operated at 630 nm, 111nW/cm$^2$ for a constant energy dose of 100J/cm$^2$.

| Photosensitizer Preparation | M.E.D. (mg/kg) | Evans Blue Increase (%) | S.D. ± | p | Dose Range Tested (mg/kg) |
|---|---|---|---|---|---|
| PHE (1) | 15 | 38 | 8.88 | <0.05 | |
| PHE (2) | 20 | 22 | 8.72 | <0.05 | |
| PHE (3) | 18 | 29 | 7.46 | <0.02 | |
| PHOTOFRIN I | 3 | 58 | 6.34 | <0.001 | |
| PHOTOFRIN II | 10 | 34 | 6.08 | <0.02 | |
| Methylene Blue | — | — | — | | 10–60 |
| ZPS[1] | 22 | 30 | 7.09 | <0.02 | |
| TPPS[2] | 2.5 | 84 | 9.58 | <0.05 | |

[1] 650 nm
[2] 640 nm

The Evans blue assay method assumes that the primary site of photodamage is the vascular system and uses Evans blue (colloidal dye) extravasation through damaged vascular wall into surrounding tissues to measure the relative phototoxicity as the minimum effective dose (M.E.D.) of photosensitizer necessary to cause a statistically significant increase in tissue Evans blue content. The higher the dose of photosensitizer required the lower the phototoxicity. The data shows that PHE preparations are relatively low in phototoxicity in this assay system. It is noted that for both PHE and Photofrin the relative phototoxicity is decreased at higher doses. This is possibly due in site aggregation and inhibition of the photosensitized reaction.

The effectiveness of PHE preparations for tumor photodynamic therapy is also assessed. Five assays are used to compare the tumor phototherapy effect of PHE preparations to Photofrin II. Four in vivo assays are used to study the effect of photosensitizer dose on tumor growth (I) growth delay (tumor experimental doubling time); (ii) regrowth delay (time for palpable tumors to occur in 50% of treated animals); (iii) local tumor control (% tumor "cures" at 30 days); and (iv) tumor cell viability (reimplant takes). The fifth assay determines total cell survival in vitro.

Figure 10:
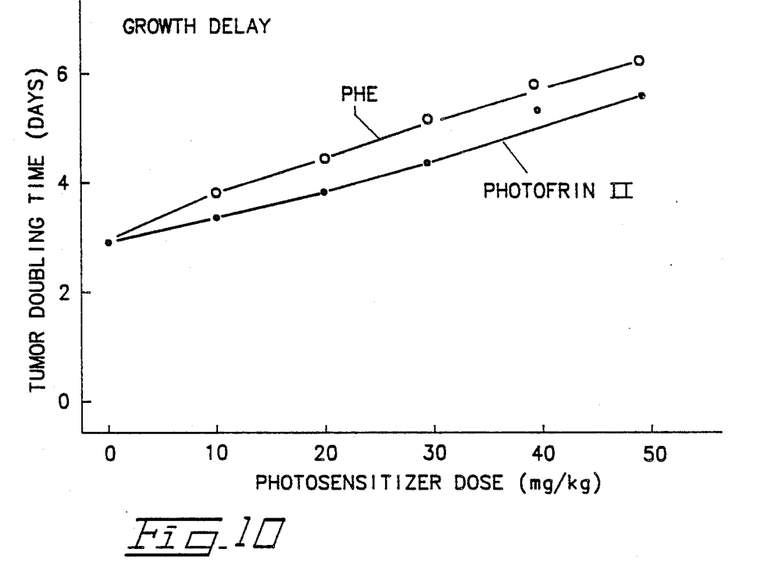
FIG. 10 is a graph comparing the effect on tumor doubling time of a composition of this invention with that observed with a material of the art.
Figure 11:
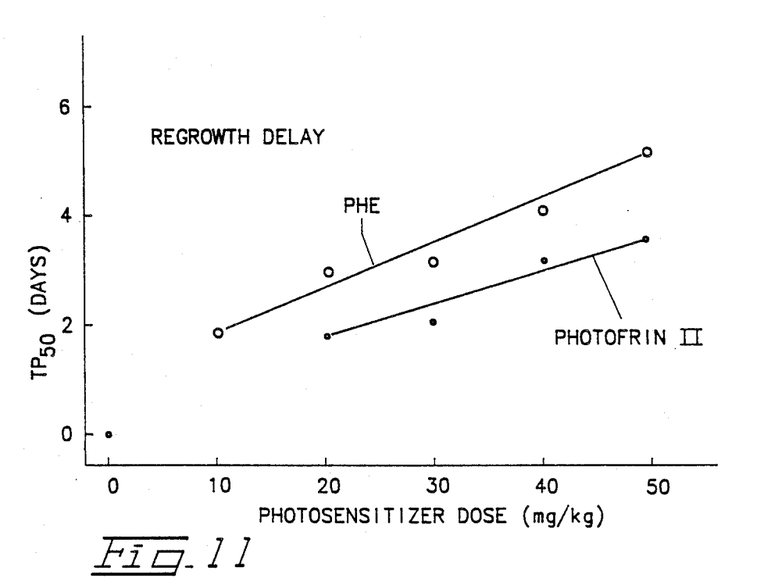
FIG. 11 is a graph comparing the effect on tumor regrowth of a composition of this invention with that observed with a material of the art.
Figure 12:
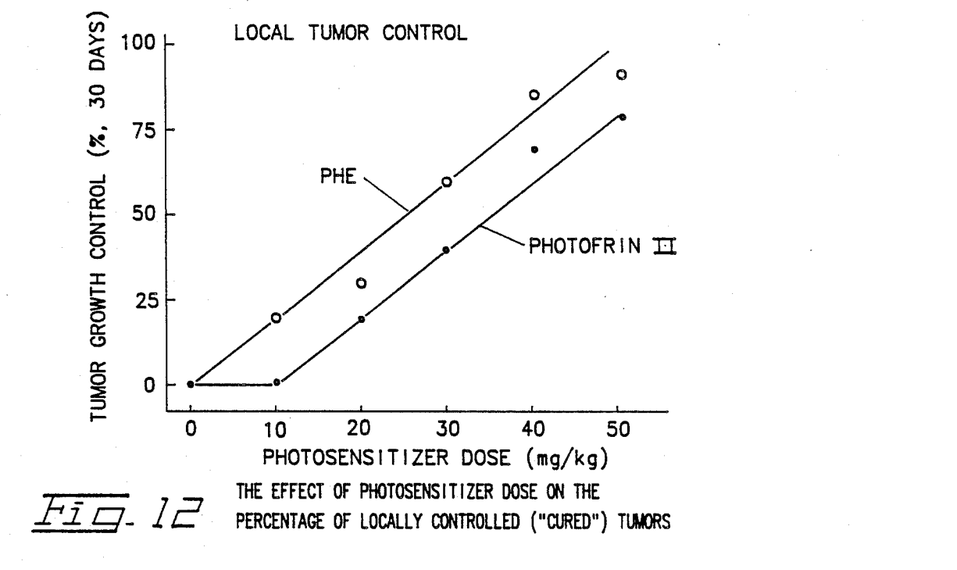
FIG. 12 is a graph comparing the effect on local tumor control of a composition of this invention with that observed with a material of the art.
Figure 13:
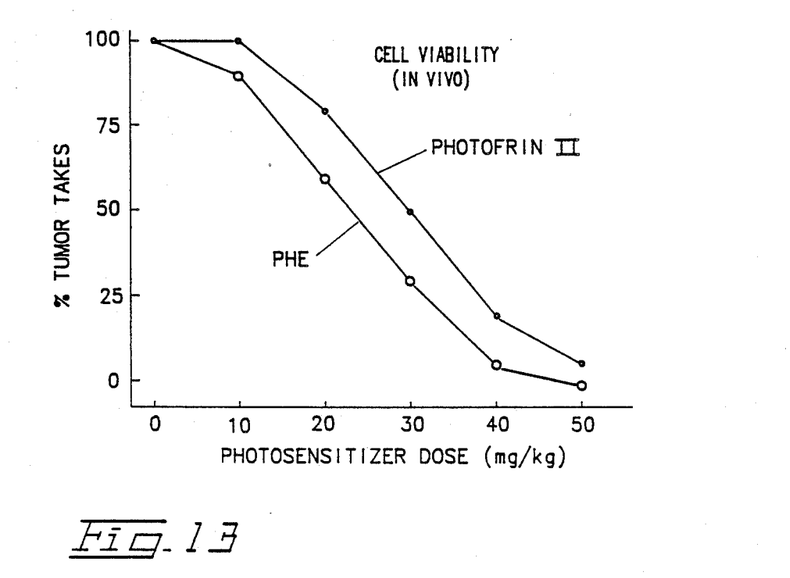
FIG. 13 is a graph comparing the effect on tumor cell viability of a composition of this invention with that observed with a material of the art.
Figure 14:
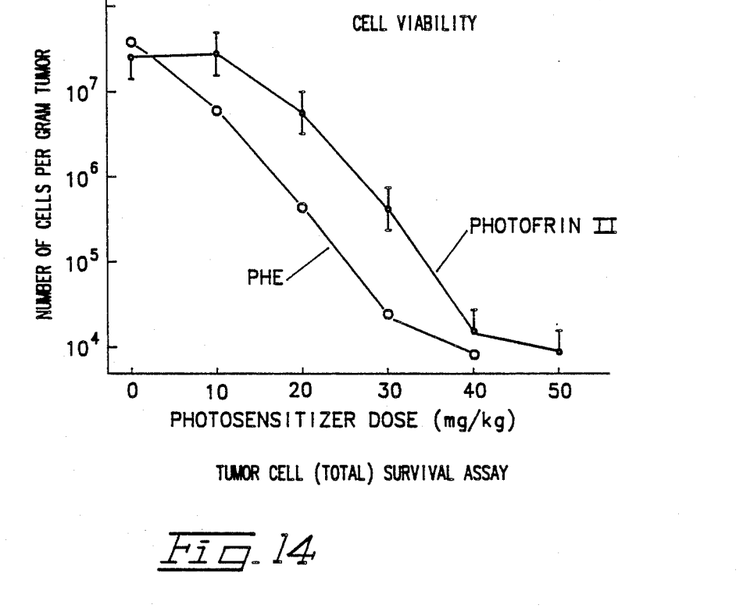
FIG. 14 is a graph comparing the effect on tumor cell viability in a second test of a composition of this invention with that observed with a material of the art.

The tumor growth kinetics of S180 growing as a solid tumor in Swiss-Webster mice have been worked out and the tumor doubling time of untreated tumor is 2.67 days. Experimental doubling times as a function of photosensitizer dose is used to assay growth delay as a result of photodynamic therapy. FIG. 10 compares the growth delays observed with PHE and Photofrin when the effect of photosensitizer dose on tumor (S180) doubling time in Swiss-Webster mice injected intraperitoneally with photosensitizer was measured. The light dose was 200J/cm$^2$. The mean doubling time of untreated S180 tumor was 2.67±0.46 days as measured between days 4 and 8. The size of each tumor was determined by excising it and measuring wet weight and using the mean of five tumor weights at day 4 and day 8 from control and treated tumors. The experiments doubling time was calculated. Each value is the mean of two experiments. The data suggest PHE appears to be more effective than Photofrin II. The same conclusion can be made from FIG. 11 showing in situ regrowth delay as measured by the time for tumors to regrow to palpable size in 50% of treated animals ($TP_{50}$). In that test, the effect of photosensitizer dose (intraperitoneal) on the number of days required for tumors (S180) to reach a palpable size (palpated daily) in 50% of treated mice (10-Swiss-Webster) was measured. Light dose was 200J/cm$^2$. Each point is the mean of two experiments. S180 tumors growing in Swiss-Webster mouse ears used as a tumor model. The superiority of the PHE preparation is further supported by FIG. 12 showing the % of 30 day tumor "cures". This test was carried out as follows. The tumors were implants (10$^7$ cells) subcutaneously on the right flank. The tumors were irradiated on day 4 (tumor diameter 4-6 mm) with Cooper Laser Sonics Aurora-Lexel Argon-Dye Laser operating at 630 nm, 200J/cm$^2$. The photosensitizer was injected intraperitoneally 24 hours before phototherapy. "Cure" was defined as the percent of mice free of palpable tumor at 30 days. The effect of PHE and Photofrin II on tumor cell viability assayed in vivo or assayed in vitro as a function of photosensitizer dose is shown in FIG. 13 and FIG. 14. The tests were carried out as follows. In the assay of FIG. B the effect of photosensitizer dose on tumor cell viability was determined by re-implantation of photodynamically treated tumors (S180) into host mice (Swiss-Webster). The light dose was 200J/cm$^2$. The tumors were excised 24 hours after phototherapy and reimplanted in host mice (5) at multiple (4) sites. The appearance of palpable tumors at within two weeks was recorded as a take. In the assay of FIG. 14, survival was measured 24 hours after irradiation with 630 nm light (200 mW/cm$^2$), 200J/cm$^2$ energy dose. Each value is the mean (+ standard error mean) of five tumors. The tumors (S180) were implanted (10$^6$ cells) subcutaneously in Swiss-Webster mice (flank). The mice were injected with photosensitizer (intraperitoneally) when the tumors were 4-6 mm in diameter. The tumor was irradiated 24 hours after injection of photosensitizer. The tumor was excised (24 hours after irradiation), weighed (wet), minced and disaggregated with proteolytic enzymes. Viable (trypan blue exclusion) cells were counted and the total number of cells per gram of tumor calculated. Again the PHE preparations are more effective at lower doses in destroying tumor cells than Photofrin II. The effect on cell viability is measured in vitro of the PHE materials shown in Table 5, as well.

TABLE 5

CELL VIABILITY TUMOR CELLS PER GRAM TUMOR
($\times 10^6 \pm$ SD)

Tumors were irradiated at day 4 after implant of $10^7$ cells subcutaneously on the right flank with Cooper Laser Sonics Aurora Lexel Argon-Dye Laser operated at 630 nm (22nW/cm$^2$) with an energy dose of 200J/cm$^2$. The irradiation was carried out 24 hours after injection of photosensitizer. Tumors were excised, weighed, minced and enzymatically disaggregated and viable (trypan blue) cells counted 24-hours after irradiation. The tumors were 406 mm in diameter and weighed 0.3–0.8 g. Each value is the mean and standard deviation of five tumors.

| Dose (mg/kg) | Photofrin I | Photofrin II | PHE (1) | PHE (2) | PHE (3) |
| --- | --- | --- | --- | --- | --- |
| 0 | 36 ± 3 | 32 ± 4 | 29 ± 5 | 32 ± 4 | 35 ± 6 |
| 5 | 33 ± 3 | 30 ± 2 | 32 ± 3 | 29 ± 3 | 29 ± 2 |
| 10 | 30 ± 6 | 29 ± 2 | 11 ± 6 | 8 ± 4 | 8 ± 2 |
| 20 | 14 ± 4 | 7 ± 2 | 0.9 ± 4 | 0.8 ± 0.3 | 0.7 ± 0.4 |
| 30 | 9 ± 5 | 0.05 ± 0.1 | 0.1 ± 0.04 | 0.09 ± 0.02 | 0.04 ± 0.01 |
| 40 | 0.7 ± 0.3 | 0.02 ± 0.01 | 0.04 ± 0.01 | $<10^4$ | $<10^4$ |
| 50 | 0.08 ± 0.01 | $<10^4$ | $<10^4$ | $<10^4$ | $<10^4$ |

What is claimed is:

1. A process for preparing a storage-stable carboxyhydroxyporphin-based product, said carboxyhydroxyporphin having from one to three inclusive carboxys and from one to three inclusive hydroxys per porphin ring, which process comprises the step of heat-treating a pH 5 to pH 9 buffered aqueous solution of said carboxyhydroxyporphin at a temperature of from 60° C. to 120° C. for a time in the range of from about 5 to about 100 hours sufficient to form a product in which at least about 80% of the carboxyhydroxyporphin is a storage-stable porphinbased oligomer.

2. The process of claim 1 wherein the carboxyhydroxyporphin comprises a carboxyhydroxychlorin.

3. The process of claim 1 wherein the carboxyhydroxyporphin comprises a carboxyhydroxyporphyrin.

4. A process for preparing a storage-stable hematoporphyrin-based product which process comprises the step of heat-treating a buffered pH 5 to pH 9 aqueous solution comprising at least about 0.1% by weight of a hematoporphyrin compound at a temperature of from about 60° C. to about 120° C. for a period in the range of from about 5 hours to about 100 hours adequate to yield a product in which at least about 80% of the hematoporphyrin compound is a storage-stable hematoporphyrin-based oligomer.

5. The process of claim 4 wherein the hematoporphyrin compound comprises hematoporphyrin derivative.

6. A process for preparing a storage-stable hematoporphyrin-based product which process comprises the step of heat-treating a buffered pH 5 to pH 9 aqueous solution comprising from about 0.1% to about 2.5% by weight of hematoporphyrin at a temperature in the range of from about 75° C. to about 125° C. for a period in the range of from about 5 hours to about 100 hours adequate to yield a product in which at least about 80% of the hematoporphyrin is a storage-stable hematoporphyrin oligomer.

7. The storage-stable carboxyhydroxyporphin oligomer product which is formed by the process of claim 1.

8. The storage-stable hematoporphyrin-based product which is formed by the process of claim 4.

9. The storage-stable hematoporphyrin-based product which is formed by the process of claim 5.

10. The storage-stable hematoporphyrin-based product which is formed by the process of claim 6.

11. A storage-stable carboxyhydroxyporphin-based pharmaceutical preparation comprising the product of claim 7 in a pharmaceutically acceptable injectable liquid carrier.

12. A storage-stable hematoporphyrin-based pharmaceutical preparation comprising the product of claim 8 in a pharmaceutically acceptable injectable liquid carrier.

* * * * *